United States Patent [19]

Klokkers-Bethke et al.

[11] Patent Number: 5,370,862
[45] Date of Patent: Dec. 6, 1994

[54] PHARMACEUTICAL HYDROPHILIC SPRAY CONTAINING NITROGLYCERIN FOR TREATING ANGINA

[75] Inventors: Karin Klokkers-Bethke; Ulrich Münch, both of Monheim/Rhld., Germany

[73] Assignee: Schwarz Pharma AG, Monheim, Germany

[21] Appl. No.: 989,987

[22] Filed: Dec. 11, 1992

Related U.S. Application Data

[63] Continuation-in-part of Ser. No. 709,581, Jun. 3, 1991, abandoned.

[30] Foreign Application Priority Data

Jun. 13, 1990 [DE] Germany .............................. 4018919

[51] Int. Cl.$^5$ ............................................... A61K 9/12
[52] U.S. Cl. .............................. 424/47; 128/200.13; 128/200.14; 141/20; 215/247; 222/394; 424/45
[58] Field of Search ............... 424/45, 47; 128/200.13, 128/200.14; 215/247; 141/20; 222/394

[56] References Cited

U.S. PATENT DOCUMENTS

| | | | |
|---|---|---|---|
| 3,155,574 | 11/1964 | Silson et al. | 424/45 |
| 4,349,135 | 9/1982 | Busselet | 222/394 |
| 4,440,777 | 4/1984 | Zupan | 424/45 X |
| 4,487,334 | 12/1984 | Werding | 222/55 |
| 4,621,964 | 11/1986 | Radtke et al. | 413/9 |
| 4,744,495 | 5/1988 | Warby | 222/402.16 |
| 4,752,466 | 6/1988 | Saferstein et al. | 424/46 |
| 4,895,719 | 1/1990 | Radhakrishnan et al. | 424/45 |
| 5,047,230 | 9/1991 | Nagy et al. | 424/45 |
| 5,125,466 | 6/1992 | Felt et al. | 177/207 |

FOREIGN PATENT DOCUMENTS 0310910 9/1988 European Pat. Off. .
62-275184 11/1987 Japan .

OTHER PUBLICATIONS

Merck Index, 10th ed., Windholz et al. (1983) p. 1095, 7456 *Poltyef*.

*Primary Examiner*—Thurman K. Page
*Assistant Examiner*—Robert H. Harrison
*Attorney, Agent, or Firm*—Marshall, O'Toole, Gerstein, Murray & Borun

[57] ABSTRACT

A pharmaceutical aerosol spray for treating an angina attack including a container having a liquid composition therein comprising 0.1 to 2 weight percent of nitroglycerin, 2 to 60 weight percent of ethanol, 2 to 60 weight percent of propylene glycol, 10 to 50 weight percent of dichlorodifluoromethane and 30 to 70 weight percent of dichlorotetrafluoroethane, the container having a valve assembly sealed to the container around an opening in the container by a sealant material which has a nitroglycerin absorption value less than 10 mg/1 g of sealant material.

10 Claims, 1 Drawing Sheet

PHARMACEUTICAL HYDROPHILIC SPRAY CONTAINING NITROGLYCERIN FOR TREATING ANGINA

This application is a continuation-in-part, of application Ser. No. 07/709,581, filed Jun. 3, 1991, abandoned.

This invention pertains to a liquid nitroglycerin spray, desirably having a hydrophilic base, and a sealant material for a container having the spray composition therein and which sealant contacts the spray composition, the nitroglycerin absorption value of the sealant being less than 10 mg of nitroglycerin per one gram of sealant material.

BACKGROUND OF THE INVENTION

Nitroglycerin, also called glycerol trinitrate or GTN, is an active substance for the treatment of angina pectoris attacks. Among other things, it is used in emergencies when the medication should be fast acting.

The pharmaceutical agents used for this specific purpose, such as sublingual tablets or crunchable capsules, have disadvantages. A disadvantage, amongst others, is that after intake the active agent in these pharmaceutical agents must first be released and dispersed prior to being available for resorption in dissolved form. Furthermore, the loss of time needed to take the pharmaceutical agent out of a blister package can be critical during an acute angina attack.

To avoid the disadvantages of the described pharmaceutical forms, nitroglycerin-containing sprays have been developed. By spraying a dose of the active agent into the buccal area of the mouth, a direct and rapid dispersion of a solution of the active agent over as large a portion as possible of the oral mucosa, which absorbs the active agent nitroglycerin was to be achieved. In this way, a large area was to be reached, thereby accelerating absorption of the active agent.

The previously known nitroglycerin pharmaceutical solutions are characterized by high vapor pressure, solution properties, and an explosive nature which have limited their use and acceptance. Therefore, a desensitized active agent—supplementary agent mixture has to be used for safety reasons during the formulation of the pharmaceutical agent spray.

Based on its lipophilic characteristics, nitroglycerin is readily soluble in solvents such as ether, acetone, ethylacetate, benzol, chloroform and triglycerides. On the other hand, the solubility of nitroglycerin in hydrophilic solvents, such as water, is limited. The solubility of nitroglycerin in water amounts to merely about 1.1 mg/ml.

Because of the low solubility of nitroglycerin in water the solvents used in the customary spray formulations are lipophilic, i.e. oils or triglycerides. However, the lipophilic solvents prevent dispersion of the active agent nitroglycerin into the hydrophilic mucosa with the desired speed during acute angina pectoris attacks.

Previously, if it was desired to increase the availability of an active agent, the amount of the lipophilic solvent was reduced. However, the nitroglycerin surge duration, measurable via the maximum plasma nitroglycerin glycerin concentration ($C_{max}$) and the time of the maximum concentration ($t_{max}$), was only insignificantly affected.

It is reported that P.M. Dewland et al [Heart and Vessels, 7, 536–544 (1987)] obtained higher $C_{max}$ values (Table 1) for three nitroglycerin sprays, manufactured with lipophilic solutions, by decreasing the amount of the lipophilic formulation portions; however, the $t_{max}$ is not significantly different.

Another way to increase the availability of the active agent is described in the DE-A 32 46 081. That reference discloses increasing the propellant portion to 60–95% by weight of the formulation. The increased propellant portion effects a higher concentration of the active agents in non-volatile oily solvents. Furthermore, the active agent must first diffuse in the mucosa from the oily active agent solution. However, the surge of the active agent, which is important when the angina attack occurs, cannot be significantly shortened. Also, for reasons of increased environmental consciousness, it is undesirable to increase the amount of propellant, so this should be avoided.

A qualitatively significant improvement in treating an angina attack is not possible if lipophilic solvents are retained in the spray.

Another starting point for quickly dispersing the active agent in the hydrophilic mucosa, is the use of a solution with dissolving characteristics which are as small as possible for the active agent nitroglycerin. In this regard, it is necessary to take into consideration that the spray formulation solution or solution mixture desensitizes the active agent nitroglycerin sufficiently and also that the solution be technically easy to handle with respect to production requirement.

U.S. Pat. No. 3,155,574 describes a nitroglycerin spray formulation-for inhalation using a hydrophilic solution base containing the active agent nitroglycerin, 1,2-propanediol and ethanol free of water, but actual exemplified embodiments of the primary packaging means are missing. However, inhalation is rather detrimental to a patient during the occurrence of an angina attack since it is more difficult to carry out. More desirable are nitroglycerin-containing sprays in which the active agent is sufficiently absorbed through the oral mucosa, so that inhalation of the active agent is not necessary.

Investigations by H. Laufen et al, reported in Therapy Week, 34, 963–970 (1984) indicated that when a hydrophilic formulation, as compared to nitroglycerin-containing sprays using a lipophilic base, is used the amount of the active agent in the blood, as well as the amount of the absorbed substance, is faster and greater than when a lipophilic base is used. The authors report use of a pump spray for dosing the solution. We know from general experience that pump sprays presently do not meet the requirements for administering pharmaceutical agents so that the formulation or composition of Laufen et al having the described therapeutically beneficial effect cannot be converted into a useful pharmaceutical agent.

The EP-A 0 310 910 describes a nitroglycerin-containing spray formulation which, besides the active agent, contains only ethanol and water as a solvent and is adjusted to a pH value of 2.4 to 6.7. However, during evaporation of the ethanol the active agent in this formulation experiences a phase separation from the water and thus is not present in a desensitized form, even though desensitization actually is desirable for safety reasons.

The present state of technology with respect to sprays having a hydrophilic base, as compared to those having a lipophilic base, reveals shortcomings, such as an absorption of nitroglycerin in the valve component parts and a reduction of the dosage amount of the active agent nitroglycerin during each new or individual spray puff or shot.

SUMMARY OF TEE INVENTION

According to the invention it has been discovered that the concentration of nitroglycerin in a liquid composition can be maintained substantially steady or constant even if placed in contact with a sealant material by selecting a sealant material which has a nitroglycerin absorption value of less than 10 mg of nitroglycerin per one gram of sealant material.

More specifically, the invention provides a product comprising a container having a liquid composition therein containing nitroglycerin, said container including a sealant material which absorbs less than 10 mg of nitroglycerin per one gram of sealing material. The container can include a valve assembly, the valve assembly including sealant means which has a nitroglycerin absorption value of less than 10 mg of nitroglycerin per one gram of sealant material. The container can include a suitable propellant which is effective for producing an aerosol spray of the liquid composition for medicinal purposes. The valve assembly can be of the type which provides a metered aerosol dose of the nitroglycerin in the form of a puffer shot. The liquid composition desirably is hydrophilic.

The sealant material is desirably a resilient polymeric material, and preferably a synthetic material. A sealant material which absorbs less than 10 mg of nitroglycerin per one gram of sealing material can be use in this invention as a monolithic sealing material, meaning that it has essentially solid uniformity and constitutes one undifferentiated whole mass which may be a single polymeric material or a mixture of two or more closely related or different polymeric materials. Thus, it need not be coated with, or covered by, some other material before it is acceptable for use in the invention. Specifically undesirable as a sealant are TEFLON-type polymers used alone, or as a coating on some other sealant material, because TEFLON-type polymers absorb nitroglycerin and swell when in contact with it.

DETAILED DESCRIPTION OF THE INVENTION

Figure 1:
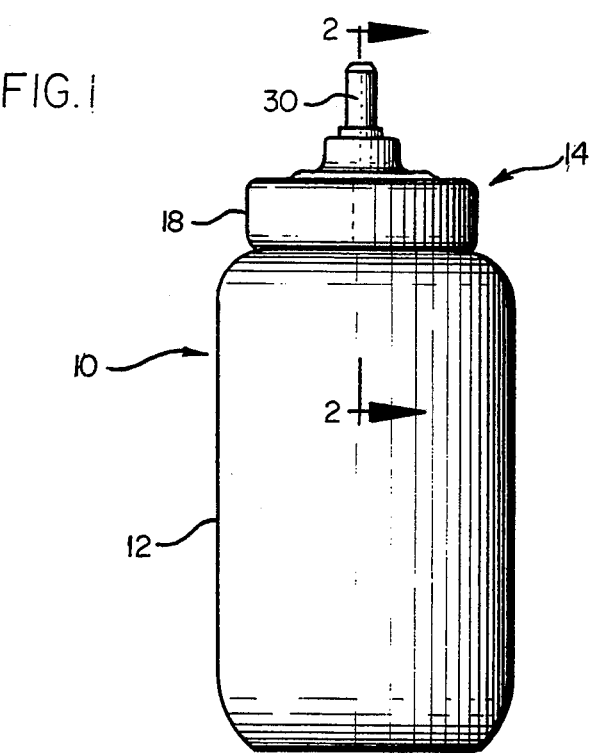
FIG. 1 is a side elevational view of one embodiment of container which can contain a hydrophilic liquid composition including nitroglycerin and which container includes a conventional valve assembly capable of dispensing a metered aerosol puff or spray of the nitroglycerin active agent.

According to a specific embodiment of the invention, a nitroglycerin aerosol spray is provided comprising a container having therein nitroglycerin, ethanol, 1,2-polyethyleneglycol, dichlorodifluoromethane and dichlorotetrafluoroethane, present in certain weight ratios to one another and which is in essentially constant contact with a container sealant material, desirably a synthetic material, the absorption value of which for nitroglycerin is less than 10 mg/1 g of sealant material.

The nitroglycerin spray according to this invention is desirably in the form of a nitroglycerin dosing pressurized aerosol-forming hydrophilic liquid, desirably composed of 0.73 weight-% nitroglycerin in a hydrophilic solution of 13.83 weight-% ethanol and 7.28 weight-% 1,2-propyleneglycol and a propellant portion of 78.16 weight-%, and with this composition being in essentially constant contact with a container sealant material, the absorption value of which is less than 10 mg of nitroglycerin per one gram of sealant material, and particularly is in the range of 0.1 to 9.9 mg of nitroglycerin per one gram of sealant material.

Besides the previously mentioned main component parts, the nitroglycerin spray according to this invention may contain the customary additives such as, for example, a nitroglycerin desensitization agent selected from the group consisting of a water soluble alcohol, glycerin and diethyleneglycol, flavoring and/or fragrance materials, which are well known to those skilled in the art.

The nitroglycerin spray according to this invention is manufactured by preparing a homogeneous one-phase solution of nitroglycerin, ethanol and 1,2-propyleneglycol and filling it into an open mouth aerosol spray container, i.e. can or bottle, at a weight-% ratio such as stated in Table 2, a suitable dosing valve assembly is crimped or swaged on and the completed closed container is then charged with a mixture of dichlorodifluoromethane and dichlorotetrafluoroethane at a weight-% ratio such as also stated in Table 2. The sealant materials in the completed product have a nitroglycerin absorption value of less than 10 mg per one gram of sealant material. The container has a height of about 63 mm and a diameter of about 22 mm. It provides about 150 puffs. Table 1 provides pharmacokinetic parameters of various prior art nitroglycerin-containing sprays, as well as of a spray (Formula XS) according to the invention, following sublingual application.

Table 2 sets forth prior art spray formulations and a spray formulation according to this invention.

The composition of a specific hydrophilic liquid spray according to this invention is as follows:

| SPECIFIC FORMULA XS | |
|---|---|
| COMPONENT | AMOUNT IN GRAMS IN 100 G OF SOLUTION |
| Nitroglycerin | 0.73 |
| Ethanol | 13.83 |
| 1,2-Propyleneglycol | 7.28 |
| Dichlorodifluoromethane | 31.26 |
| Dichlorotetrafluoroethane | 46.90 |
| Sealant material with an absorption value for nitroglycerin below 10 mg/1 g of sealant material | |

Hydrophilic liquid spray compositions provided by the invention will usually be within the following formulas:

| BROAD FORMULA XB | |
|---|---|
| COMPONENT | AMOUNT IN GRAMS IN 100 G OF SOLUTION |
| Nitroglycerin | 0.1 to 2 |
| Ethanol | 2 to 20 |
| 1,2-Propyleneglycol | 2 to 30 |
| Dichlorodifluoromethane | 10 to 40 |
| Dichlorotetrafluoroethane | 30 to 50 |
| Sealant material with an absorption value for nitroglycerin below 10 mg/1 g of sealant material | |

| BROAD FORMULA XC | |
|---|---|
| COMPONENT | WEIGHT PERCENT |
| Nitroglycerin | 0.1 to 2 |
| Ethanol | 2 to 60 |
| 1,2-Propyleneglycol | 2 to 60 |
| Dichlorodifluoromethane | 10 to 50 |
| Dichlorotetrafluoroethane | 30 to 70 |
| Sealant material with an absorption value for nitroglycerin below 10 mg/1 g of sealant material | |

The hydrophilic liquid spray composition in the finished product is in contact with the container sealant material, and particularly the dosage metering valve materials.

Stability investigations of sprays with identical contents according to this invention, identical containers, but qualitatively different valve assemblies revealed that the pharmaceutical quality of the product is only maintained by the use of valve assemblies which have been manufactured of specific sealant materials in which no, or only a tolerable, absorption of the nitroglycerin occurs in the valve assembly component parts.

Referring now to the drawings, FIG. 1 illustrates a finished product 10 according to the invention. The product 10 includes an open-mouth container body or preform 12 on which a valve assembly 14 has been attached by crimping or swaging. It should be understood that the invention is not limited to use of any particular container or valve assembly. The specific embodiment illustrated by the drawings is presented to show where sealant materials are located in such spray products and thereby contact the liquid nitroglycerin product.

Figure 2:
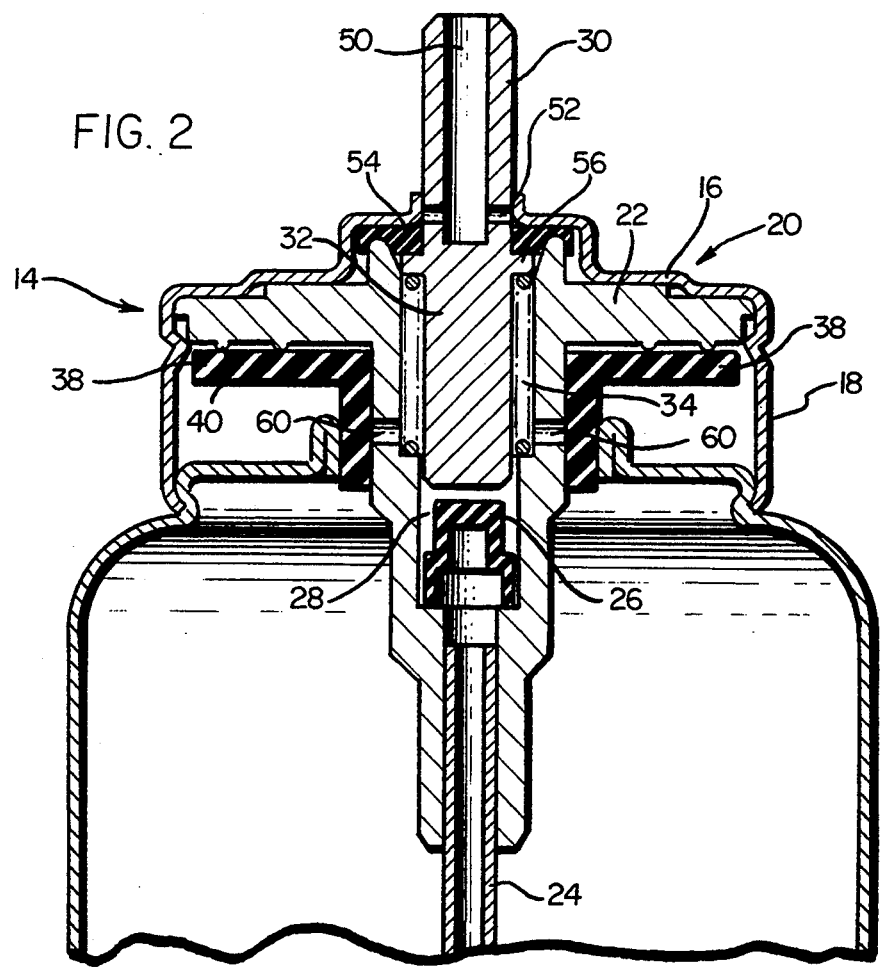
FIG. 2 is a vertical sectional view taken along the line 2—2 of FIG. 1 and shows the valve assembly included in the container illustrated in FIG. 1.

The valve assembly 14 is shown in vertical cross-section in FIG. 2. The valve assembly 14 includes a cup 16 which has a vertical cylindrical skirt 18 and a top 20. Valve body 22 fits within the cup 16. A tube or standpipe 24 fits within the lower end of valve body 22 and extends to adjacent the bottom of the container body 12. A vertically displaceable loosely positioned plug 26 is located within an axial bore 28 in valve body 22. The plug 26 is made of a resilient sealant material so that it can seal readily with the bottom of axial bore 28 in valve body 22 when a metered dose is being expelled. Valve stem 30 has a lower solid portion 32 which fits into bore 28. A spring 34 is positioned between the wall of bore 28 and the surface of stem portion 32. The spring 34 presses against the stem flange 56 and against a ledge near the bottom of the bore 28. A gasket 38, which is L-shaped in section, fits securely against the valve body 22 and the outwardly projecting flange 40 contacts the valve body 22 to provide a fluid tight seal. The gasket 38 is made of sealant material.

The upper end of valve stem 30 has a vertical axial hole 50 and a pair of horizontal holes 52 which penetrate the wall of the stem into communication with the hole 50. A valve seat 54, made of sealant material, is located in the too 20 so as to be around the stem 30 upper portion. It prevents upward movement of the stem 30 when the stem flange 56 contacts the valve seat 54. Such contact provides the ultimate seal which prevents escape of fluid from the container after it is filled, such as to an internal pressure of 4 bar, and is not in use. The two horizontal holes 60 are used to fill the container with propellant.

When the container is filled and not in use the internal pressure causes the plug 26 to lift upwardly so that liquid fills the space in the valve body 22 above plug 26. When a metered dose is to be administered the top of stem 30 is pushed down causing the lower end of the stem to force plug 26 into sealing position with the bottom of bore 28. This prevents liquid from flowing into bore 28 from the container body during the period when a metered dose is expelled as a puff or shot into the buccal area of a person's mouth. Shortly after the plug 26 is pressed into sealing position as described, the holes 52 are positioned below valve seat 54 thereby permitting liquid to flow from bore 28 into the holes 52 and then into hole 50 from which it exits as an aerosol metered puff.

Table 3 shows the interaction of the critical valve component parts, that is the identified sealants and a liquid spray composition therein according to this invention. Absorption of the active agent into the resilient polymeric monolit sealant material was determined by quantification of the nitroglycerin following its extraction from the valve sealant material after a two or four week storage period in contact with the spray solution.

The WE number (Table 3) is an identity number of the valve from which the respective sealing material was taken. During manufacture of the spray solution according to the invention, a specified amount of sealant material was added to the solution of active agent in the spray container, a valve was crimped on, the container charged, and the spray stored upright under the appropriate condition. At the time of testing, the spray container was discharged or emptied in a cooled condition, the sealant material removed, washed, and the nitroglycerin content determined after the extraction. The tests resulted in the values shown in Table 3.

The nitroglycerin (GTN) absorption at 20° C. amounts to 53 mg GTN/1 g sealant No. 400; 45 mg GTN/1 g buna BA 170 T.; 3.4 GTN/1 g neoprene beige and $\leq$1 mg GTN/1 g butyl FA 7500. Neoprene is a polymer produced from 2-chloro-butadiene and is available from Dupont, Wilmington, Del; butyl FA 7500 is supplied by Action Technology S.p.A., IT-20063 Gaggiano (MI), Via Alessandro Volta 76, Italy, which also has factories in Rockaway, N.J., Clinton Ill. and Anaheim, Calif.

Neoprene beige is available from Action Technology under the tradename Neopren AK/B. However, not all neoprene polymers are suitable. Thus, Neopren K3G, a type of neoprene, available from Action Technology is not suitable in the spray container of this invention.

Valves with sealant materials having an absorption value greater than 10 mg/1 g sealant material, following storage in contact with the spray, led to an active agent reduction in the package such that the active ingredient content per individual dosage fell below the limits of the guidelines accepted by the German Pharmaceutical Law Code. Furthermore, valve assemblies with these strongly absorbing sealant materials, in the area of the dosing chamber, have contact with the next dose to be dispersed, thus further leading to unacceptably low dosage concentrations.

Tables 4 and 5 show this absorption phenomenon at four charges of sprays which had been manufactured with valve assemblies containing different sealant materials. The tables report the amount of active agent as a percent of the predetermined or set dosage amount in the first, second and third individual spray shots or puffs following varying nonuse time intervals. Only valve assemblies which contain butyl FA 7500 and neoprene provided acceptable pharmaceutical quality.

Thus, practical dispensing of the pharmaceutical agent requires the use of dosage valve assemblies which employ specific sealant materials.

Furthermore, the varying distribution coefficient (Pu) of nitroglycerin between the components of the pharmaceutical formulation (R) and the hydrophilic oral mucosa (M) where $$Pu = \frac{M}{R}$$

is larger in the case of the hydrophilic formulation than in the case of a lipophilic formulation, through which the fast surge in vivo is achieved, is decisive.

The distribution $$P_k = \frac{D}{R} \text{ (sealant} = D\text{)},$$

that is, in identical sealants is then larger in the case of the hydrophilic sprays and necessitates the use of new, specific sealant materials which have a low solubility, or a lower absorption, for nitroglycerin.

In a bio-availability study and in a clinical study, the intended faster surge of the active agent with the nitroglycerin dosage spray according to this invention was documented and the faster effect shown, as compared to the slower lipophilic spray.

Of significance therapeutically is a fast surge ($t_{max}$) to high active agent concentrations. The medication of this invention acts fast and effectively. Associated with this fast action is an earlier arrest of the angina pectoris attack and a rapid relief for the patient in this life threatening situation fraught with mortal terror.

Two differently formulated nitroglycerin sprays were compared with one another using the same method of administration.

The test spray (T) is a spray having the specific composition set forth above according to this invention with the specific sealant material, which contains the active agent in a hydrophilic solution. The reference spray (R) contains the active agent in a lipophilic solution. Table 6 shows the result of the testing.

TABLE 6

| Parameter | T | R | T/R | P |
|---|---|---|---|---|
| $C_{max}$ [pg/ml] | 1774 ± 1272 | 884 ± 693 | 2.16 | 0.006 |
| $t_{max}$ [min] | 4.4 ± 1.4 | 7.9 ± 2.8 | | <0.05 |
| AUC [pg min/ml] | 9488 ± 5303 | 6990 ± 5168 | 1.52 | n.s. |

The test results reported in Table 6 reveal that the active agent from the test preparation was absorbed significantly faster than from the reference spray; $C_{max}$ was higher by the factor 2.2, and $t_{max}$ was shortened from 7.9 to 4.4 min.

The spray according to this invention provides a pharmaceutical product of good quality and which produces a fast surge of the active agent. For an angina pectoris patient, this means a faster effect and an earlier alleviation or removal of the anxiety state which occurs during an attack.

TABLE 1

Summary of Pharmacokinetic Parameters of Various Nitroglycerin Sprays Following Sublingual Application

| Drug | Source No. (See Footnotes) | Number of Tests | Dose | $C_{max}$ (pg/ml) | $t_{max}$ (min) | AUC (min pg/ml$^{-1}$) | rel. AUC (%) |
|---|---|---|---|---|---|---|---|
| Lipophilic Spray A | 1A | 3 | 0.4 | 1. 400<br>2. 860<br>3. 590 | 4–5<br>3<br>5 | — | |
| Lipophilic Spray B | 1B | 3 | 0.4 | 1. 2260<br>2. 1620<br>3. 1444 | 3.2<br>6.5<br>10.0 | — | |
| Lipophilic Spray C | 2 | 12 | 0.8 | 670 ± 500 | 10.0 | 5740 ± 4590 | 56.26 |
| Lipophilic Spray D | 2 | 12 | 0.8 | 760 ± 450 | 8.0 | 6360 ± 3970 | 58.9 |
| Lipophilic Spray B | 2 | 12 | 0.8 | 1150 ± 770<br>p < 0.05 | 8.0<br>p > 0.05 | 9990 ± 8080<br>p < 0.05 | 100 |
| Lipophilic Spray A | 3 | 8 | 0.8 | 780 ± 850 | 7 | 1369 ± 16040 | 36.5 |
| Hydrophilic Spray A | 3 | 8 | 0.8 | 3810 ± 2810 | 4 | 37460 ± 14640<br>< 0.05 | 100 |
| Lipophilic Spray B | 4 | 12 | 0.8 | 340 ± 234 | 8.3 ± 2.0 | 3516 | 36.9 |
| Hydrophilic Spray B | 4 | 12 | 0.8 | 1387 ± 630<br>p < 0.001 | 4.3 ± 1.6<br>p < 0.05 | 9534<br>p < 0.001 | 100 |
| Lipophilic Spray B | 5A | 24 | 0.4 | 884 ± 693 | 7.9 ± 2.8 | 6990 ± 5158 | 73 |
| Spray according to this Invention Formula XS | 5B | 24 | 0.4 | 1774 ± 1272<br>p = 0.006 | 4.4 ± 1.4<br>p > 0.05 | 9488 ± 5303<br>Insignificant | 100 |

TABLE 1 - FOOTNOTES
1A. Nitrolingual Spray from 1982 produced by German firm Pohl Boskamp Company.
1B. New formulation of the Nitrolingual Spray from Pohl Boskamp Company.
2. Data from P. M. Dewland et al, Herz and Gegasse, 7, 536–544 (1987).
3. Data from H. Laufen et al in Therapiewoche 34, 963–970 (1984).
4. Data from S. W. Sanders et al J. of Pharmaceutical Sciences, 75, 244–246 (1986).
5A. Nitrolingual Spray of Pohl Boskamp Company (same spray as 1B).
5B. Spray according to the invention - Formula XS.

TABLE 2

Spray Formulations

| Drug | Lipophilic Spray A | Lipophilic Spray B | Hydrophilic Spray A | Hydrophilic Spray B | | Spray according to this Invention | |
|---|---|---|---|---|---|---|---|
| Source No. | 1 | 1 | 3 | Dictionnaire Vidale 1987 | | Formula XS | |
| Components | Grams in 100 g | Grams in 100 g | | | Ml in 100 ml | Components | Grams in 100 g |
| Nitroglycerin | 0.9 | 0.7 | Hydrophilic water miscible pump spray | Nitroglycerin 4% w/w in ethanol | 34 ml | Nitroglycerin 5% w/w in Ethanol | 14.56 |
| Neutral oil (1) | 27 | 15.0 | | | | | |
| Paraffin oil-viscous | 12.4 | — | | Ethanol 95% v/v | 14 ml | 1,2-Propyleneglycol | 7.28 |
| Ether | 2.2 | 1.8— | | Diethyleneglycol-monoethylether | 1 ml | | |
| Fragrance | 0.5 | 0.4 | | Fragrance | 1 ml | | |
| Propellant | 57.0 | 82.1 | | Dichlorodifluoro-methane | 50 ml | Dichlorodifluoro-methane | 31.26 |
| | | | | | | Dichlorotetra-fluoroethane | 46.90 |

(1) Miglyol 812 - Neutral oil; contains the nitroglycerin.

TABLE 3

Absorption of Nitroglycerin Into Various Sealant Materials From a Spray (1) of This Invention [mg Nitroglycerin/1 g Sealant]

| | Storage Conditions | | | |
|---|---|---|---|---|
| Sealant Material | 20° C. 2 Weeks | 40° C. 2 Weeks | 20° C. 4 Weeks | 40° C. 4 Weeks |
| Buna BA 170T (from valve WE 947) | 45.0 | 51.0 | 44.5 | 49.0 |
| Seal No. 400 (from valve WE 999) | 53.2 | 61.1 | — | — |
| B 470 PA (from valve WE 1010) | 56.3 | 53.6 | — | — |
| RP 3-49-16 (from valve WE 1008) | 44.0 | 49.0 | — | — |
| Neoprene, black (from valve WE 1007/1008) | 11.4 | 14.3 | 14.6 | 15.2 |
| Neoprene, beige (from valve WE 1031) | 1.5–7.5 | 6.9–7.5 | 3.4 | 13.0 |
| Butyl FA 7500 (from valves WE 1123, 1124, 1125) | — | — | 0.05–0.07 | — |

(1) Formula XS

TABLE 4

Nitroglycerin Per Spray Dosage i.e. Puff or Shot

| Product Composition Product Number Sealant Material Storage Time After Manufacture and Priming (1) [Weeks] | Spray (1) According to the Invention Spray 1 Butyl FA 7500 Nitroglycerin [%]/Three Spray Puffs | | | | Spray (1) According to the Invention Spray 2 Neoprene, free of carbon Nitroglycerin [%]/Three Spray Puffs | | | |
|---|---|---|---|---|---|---|---|---|
| | | 1st. | 2nd. | 3rd. | | 1st. | 2nd. | 3rd. |
| 2.5 | A | 74.5 | 83.2 | 89.1 | A | 76.0 | 93.3 | 99.5 |
| Storage Time 2 Terms [Weeks] | B | 75.7 | 87.8 | 91.6 | B | 78.2 | 92.0 | 97.5 |
| | | | | | C | 71.8 | 91.3 | 96.4 |
| 1 | A | 86.4 | 94.8 | 99.0 | A | 86.9 | 96.8 | 100.0 |
| | B | 83.8 | 92.2 | 98.9 | B | 86.9 | 98.9 | 100.0 |
| | | | | | C | 82.6 | 94.3 | 99.8 |
| 3 | A | 85.2 | 92.0 | 100.7 | A | 76.9 | 93.4 | 96.7 |
| | B | 83.1 | 96.7 | 98.0 | B | 79.4 | 92.0 | 96.3 |
| | | | | | C | 80.9 | 90.2 | 99.2 |
| 10 | A | 83.8 | 98.7 | 102.5 | A | 62.2 | 85.2 | 99.2 |
| | B | 98.9 | 98.0 | 97.2 | B | 58.9 | 81.4 | 93.8 |
| | | | | | C | 64.4 | 91.6 | 99.6 |

Storage conditions: 20–25° C. 40–60% relative humidity (1) Formula XS
Nitroglycerin [%]/spray puff refers to the nitroglycerin content/spray puff or shot, which was determined as a constant value after multiple valve emissions. See Table 5.
A, B, C = symbol for the spray container
(1) Priming means to load the valve and have the product contact the gasket and be ready to spray a dose or puff.

TABLE 5

Nitroglycerin Per Spray Dosage i.e. Puff or Shot

| Product Ch.-B. Sealant Material Storage Time After Manufacture and Priming [Weeks] | | Spray According to the Invention Spray 1 Buna BA 170T Nitroglycerin [%]/Three Spray Puffs | | | | Spray According to the Invention Spray 2 Sealant No. 400 Nitroglycerin [%]/Three Spray Puffs | | |
|---|---|---|---|---|---|---|---|---|
| | | 1st. | 2nd. | 3rd. | | 1st. | 2nd. | 3rd. |
| 4 | A | 56.3 | 85.0 | 92.1 | A | 69.7 | 77.4 | 81.2 |
|   | B | 55.6 | 80.9 | 94.1 | B | 72.0 | 82.0 | 86.2 |
| Storage Time 2 Terms [Weeks] | | | | | C | 69.3 | — | 86.8 |
| 1 | A | 54.0 | 83.5 | 94.2 | A | 65.0 | 75.2 | 85.3 |
|   | B | 59.5 | 82.5 | 98.5 | B | 51.5 | 69.1 | 82.3 |
| 3 | A | 48.8 | 81.8 | 94.1 | | | | |
|   | B | 48.8 | 87.7 | 104.9 | | | | |
| 10 | A | 63.5 | 87.7 | 92.7 | Seal No. 400: A nitrogen content of 100%/spray puff is reached from about 15th spray puff on | | | |
|   | B | 51.8 | — | 95.3 | | | | |

Storage condition: 20-25° C./40-60% relative humidity
Nitroglycerin [%]/spray puff refers to the nitroglycerin content/spray puff or shot, which was determined as a constant value after multiple valve emissions.
A, B, C = symbol for the spray container.

What is claimed is:

1. An aerosol spray including a closed container having a liquid composition therein comprising 0.1 to 2 weight percent of nitroglycerin, 2 to 60 weight percent of ethanol, 2 to 60 weight percent of 1,2-propyleneglycol, 10 to 50 weight percent of dichlorodifluoromethane and 30 to 70 weight percent of dichlorotetrafluoroethane, the container having a valve assembly sealed to the container around an opening in the container by a monolithic resilient polymeric sealant material selected from the group consisting of butyl FA 7500 and neoprene free of carbon.

2. An aerosol spray according to claim 1 comprising 0.73 weight percent of nitroglycerin, 13.83 weight percent of ethanol, 7.28 weight percent of 1,2-propyleneglycol, 31.26 weight percent dichlorodifluoromethane and 46.90 weight percent dichlorotetrafluoroethane.

3. An aerosol spray according to claim 1 containing a pharmaceutically acceptable nitroglycerin desensitization agent.

4. An aerosol spray according to claim 1 containing a nitroglycerin desensitization agent selected from the group consisting of a water soluble alcohol, glycerin and diethyleneglycol.

5. An aerosol spray according to claim 1 in which the sealant material comprises a gasket between the valve assembly and the container.

6. An aerosol spray according to claim 1 in which the sealant material comprises a gasket between the valve assembly and the container and the valve assembly has a manually operable spray valve for spraying a metered dosage of nitroglycerin in aerosol form into the mouth of a patient.

7. An aerosol spray according to claim 1 in which the liquid composition in the container is in essentially constant contact with the sealant material.

8. An aerosol spray including a closed container having a hydrophilic liquid composition therein comprising 0.1 to 2 g of nitroglycerin, 2 to 20 g of ethanol, 2 to 30 g of 1,2-propyleneglycol, 10 to 40 g of dichlorodifluoromethane and 30 to 50 g of dichlorotetrafluoroethane, per 100 g of liquid composition, the container having a valve assembly sealed to the container around an opening in the container by a monolithic resilient polymeric sealant material selected from the group consisting of butyl FA 7500 and neoprene free of carbon.

9. An aerosol spray, for buccal or sublingual administration of nitroglycerin, including a closed container having a hydrophilic liquid composition therein comprising 0.1 to 2 g of nitroglycerin, 2 to 20 g of ethanol, 2 to 30 g of 1,2-propyleneglycol, 10 to 40 g of dichlorodifluoromethane and 30 to 50 g of dichlorotetrafluoroethane, per 100 g of liquid composition, the container having a valve assembly sealed to the container around an opening in the container by a monolithic resilient polymeric sealant material selected from the group consisting of butyl FA 7500 and neoprene free of carbon, said composition when sprayed in metered puffs therefrom producing puffs having a substantially constant amount of nitroglycerin per puff.

10. An aerosol spray, for buccal or sublingual administration of nitroglycerin including a closed container having a hydrophilic liquid composition therein comprising 0.1 to 2 weight percent of nitroglycerin, 2 to 60 weight percent of ethanol, 2 to 60 weight percent of 1,2-propyleneglycol, 10 to 50 weight percent of dichlorodifluoromethane and 30 to 70 weight percent of dichlorotetrafluoroethane, the container having a valve assembly sealed to the container around an opening in the container by a monolithic resilient polymeric sealant material which is selected from the group consisting of butyl FA 7500 and neoprene free of carbon, said composition when sprayed in metered puffs therefrom producing puffs having a substantially constant amount of nitroglycerin per puff.

* * * * *

UNITED STATES PATENT AND TRADEMARK OFFICE
CERTIFICATE OF CORRECTION

PATENT NO. : 5,370,862

DATED : December 6, 1994

INVENTOR(S) : KARIN KLOKKERS-BETHKE and ULRICH MUNCH

It is certified that error appears in the above-identified patent and that said Letters Patent is hereby corrected as shown below:

Column 1, line 63, delete second occurrence of "glycerin"; (Specification, page 3, line 1)

Column 2, line 30, "formulation-for" should be --formulation for--; (Specification, page 4, line 5)

Column 3, line 3, "SUMMARY OF TEE INVENTION" should be --SUMMARY OF THE INVENTION--; (Specification, page 5, line 14)

Column 3, lines 25, "puffer" should be --puff or--; (Specification, page 6, line 6)

Column 3, line 30, "use" should be --used--; (Preliminary Amendment dated December 11, 1992, page 1, line 11)

Column 5, line 61, "too" should be --top--; (Specification, page 10, last line)

Column 6, line 20, "monolit" should be --monolithic--; (Preliminary Amendment dated December 11, 1992, page 2, line 16)

UNITED STATES PATENT AND TRADEMARK OFFICE
CERTIFICATE OF CORRECTION

PATENT NO. : 5,370,862

DATED : December 6, 1994

INVENTOR(S) : KARIN KLOKKERS-BETHKE and ULRICH MUNCH

It is certified that error appears in the above-identified patent and that said Letters Patent is hereby corrected as shown below:

Column 8, Table 1, line 18, "<0.05" should be --p <0.05--; (Specification, page 16, 7th grouping of numbers)

Column 11, Table 5, lower right-hand corner, "nitrogen" should be --nitroglycerin--; (Specification, page 21, lower right-hand corner)

Signed and Sealed this

Seventh Day of March, 1995

Attest:

BRUCE LEHMAN

*Attesting Officer*     *Commissioner of Patents and Trademarks*